US006931926B1

(12) United States Patent
Van Ee

(10) Patent No.: US 6,931,926 B1
(45) Date of Patent: Aug. 23, 2005

(54) LIQUID DEPTH SENSING SYSTEM WITH LIQUID IDENTIFICATION CAPABILITY

(76) Inventor: William J. Van Ee, 8975 Indian Ridge Rd., Cincinnati, OH (US) 45243-3740

( * ) Notice: Subject to any disclaimer, the term of this patent is extended or adjusted under 35 U.S.C. 154(b) by 0 days.

(21) Appl. No.: 10/825,333

(22) Filed: Apr. 16, 2004

(51) Int. Cl.[7] .............................................. G01F 23/00
(52) U.S. Cl. ........................................ 73/299; 73/291
(58) Field of Search .......................... 73/299, 301, 302, 73/864.35, 291; 340/614

(56) References Cited

U.S. PATENT DOCUMENTS

| 3,729,997 A | 5/1973 | Luke ............................ 73/302 |
| 3,987,675 A | 10/1976 | Harrison ...................... 73/302 |
| 4,297,081 A | 10/1981 | Irvin .............................. 417/2 |
| 4,984,451 A | 1/1991 | Wilen et al. ................... 73/438 |
| 5,059,954 A | 10/1991 | Beldham et al. ............ 340/614 |
| 5,163,324 A | 11/1992 | Stewart ........................ 73/302 |
| 5,953,954 A | 9/1999 | Drain et al. .................. 73/302 |
| 6,510,736 B1 | 1/2003 | Van Ee ......................... 73/299 |
| 6,513,376 B1 | 2/2003 | Stacey et al. ................. 73/299 |
| 6,539,796 B2 | 4/2003 | Shirai et al. .................. 73/299 |
| 6,647,781 B2 | 11/2003 | Su .............................. 73/299 |

FOREIGN PATENT DOCUMENTS

| DE | 19826487 | 12/1999 |
| JP | 59-073732 | 4/1984 |
| JP | 60-088324 | 5/1985 |
| JP | 60-102524 | 6/1985 |
| JP | 63-191026 | 8/1988 |
| JP | 01-074420 | 3/1989 |

OTHER PUBLICATIONS

Website, www.online-tensionmeter.com/OBERFL/Surface Tension.HTML, ®2000-2003, SITA MESSTECHNIK GMBH Describing Surface Tension Measurement Devices for Water.

*Primary Examiner*—Hezron Williams
*Assistant Examiner*—Tamiko Bellamy
(74) *Attorney, Agent, or Firm*—Richard C. Litman

(57) ABSTRACT

The present liquid depth sensing system with its liquid identification capability provides an economical device which may be installed in a multitude of different applications to perform multiple quantity measurement and detection functions. The present system includes a miniaturized piezoelectric pneumatic pump, sized and adjusted to produce a consistent stream of bubbles from the outlet end of the dip tube in the purge system of the present invention. The small variations in pneumatic pressure in the system due to the cycling of each bubble working through the surface tension and viscosity of the liquid as the bubble leaves the outlet end of the tube are detected and converted to a voltage signal which is used to identify the liquid at the outlet end of the tube. The present system is extremely valuable for identifying contaminants in the tank, as well as for measuring the liquid quantity in the tank.

20 Claims, 11 Drawing Sheets

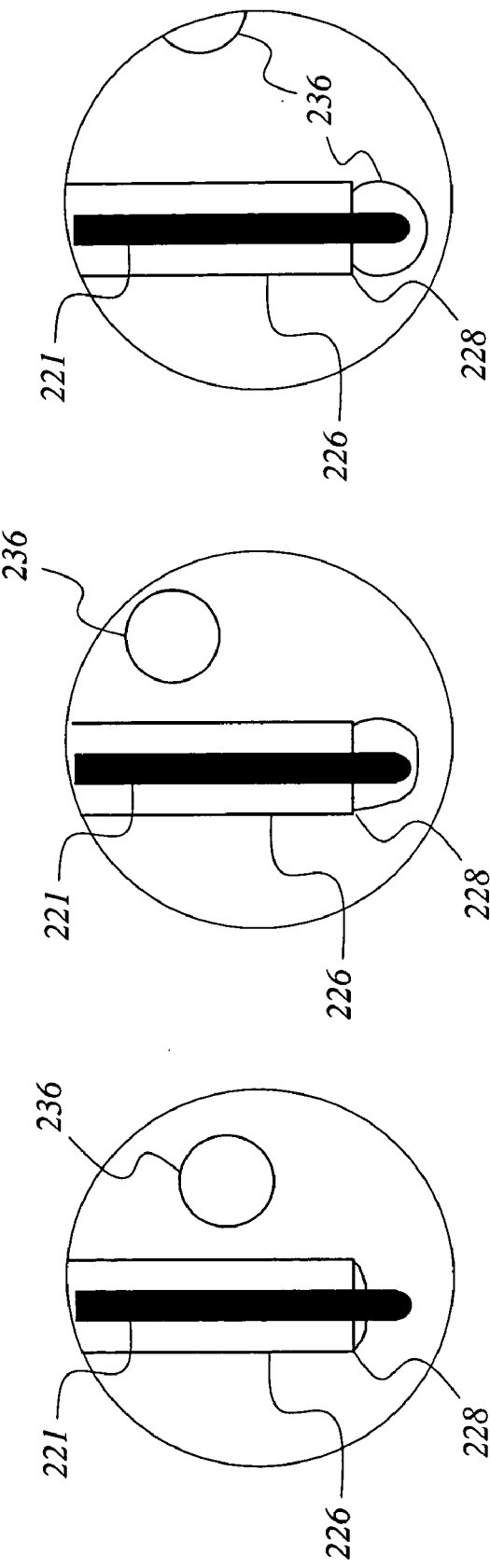

LIQUID DEPTH SENSING SYSTEM WITH LIQUID IDENTIFICATION CAPABILITY

BACKGROUND OF THE INVENTION

1. Field of the Invention

The present invention relates generally to purge or bubble tube type devices used for the measurement of the depth of a quantity of liquid. More specifically, the present invention is directed to a system using such a purge type apparatus for precisely measuring both the pressure head and the properties of the liquid at the bubble tube outlet by means of the "bubble signature," which varies due to the properties of the liquid.

2. Description of the Related Art

The purge or bubble tube principle of determining the depth of a quantity of liquid is well known. The present inventor has a previously issued (U.S. Pat. No. 6,510,736, discussed further below in greater detail) which discloses various improvements in such devices. Such purge type systems can provide various advantages in the accuracy and response times of liquid depth or level indicator systems, and are used in various different environments for rapidly and accurately filling containers in the bottling and other industries.

However, in many instances it is not only important to be able to accurately measure the quantity of a liquid, but also to be able to test the liquid for impurities or adulteration by another liquid of some other type. One field in which this is extremely critical is aviation. Water is an occasional contaminant of aviation fuels (both gasoline and turbine fuels) and its incombustibility can result in disaster if a significant quantity of water is ingested by the aircraft engine. Yet, aircraft fuel systems are quite prone to water contamination, as most aircraft spend most of their lives outside where precipitation can flow into lower areas around recessed fuel caps and thence into the fuel tanks if the caps seal less than perfectly. Water is also occasionally pumped into aircraft fuel tanks due to contamination of the fuel supply. A perhaps even more common means for water to contaminate fuel systems is through condensation in a partially filled fuel tank. Moisture will often condense on the sides of the tank and run to the bottom of the tank, due to the density of the water being greater than that of the fuel in the tank. Since the fuel pickup in a fuel tank is always at or adjacent the lowest point in the tank in order to draw all (or nearly all) of the fuel from the tank, the fuel system will draw water from the tank if there is any significant amount within the tank. As a result, it is common practice to drain a sample of fuel from each tank and low point in an aircraft before flight, in order to check for contamination of the fuel supply. Essentially the same problems can occur in fuel oil tanks used for home heating, as well as other motor vehicle tanks. The use of alcohol additives in automobile fuel tanks to dissolve ice which has frozen in the fuel lines is well known in northern climes in the winter.

However, fuel contamination can also occur due to other factors. Another example from the aviation field is the contamination of one type of fuel, e.g. aviation gasoline, with another type, e.g. jet turbine fuel. While turbine engines can run reasonably well on fuels having a relatively high percentage of gasoline mixed therewith, the reverse is not true. Any significant quantity of turbine fuel, with its relatively low octane, will lead to detonation and engine damage in a spark ignition reciprocating engine. Although great care is universally used in refueling aircraft with the proper fuel, there have been accidents in the past from time to time in which turbine fuel has been used to refuel a reciprocating engine powered aircraft.

While there are various tests available for checking the type of fuel in a tank or container, and/or checking fuel for contamination, most such means are not an integral part of the fuel system of the aircraft or other system. Rather, such tests must be carried out on the ground, generally at some specialized test site or location. Such tests do nothing to measure or determine the quantity of fuel in the tank or container, in any event.

Accordingly, what is needed is a small, inexpensive apparatus which may be integrated with a fuel or other liquid container system, which apparatus may serve to both measure the pressure head of the liquid within the container, and also to check the liquid for contamination by another liquid in the lower portion of the tank. The present invention provides such a device in the form of a purge or bubble tube type system, which serves to accurately measure the pressure head (and thus the quantity, if the tank configuration is known) of the liquid within the container or tank, and which also may be used to Distinguish between different types of liquids at the outlet of the bubble tube due to the different "bubble signatures" which result as the bubble stream enters different liquids having different surface tensions and other properties from one another.

A discussion of the related art of which the present inventor is aware, and its differences and distinctions from the present invention, is provided below.

U.S. Pat. No. 3,729,997 issued on May 1, 1973 to Owen B. Luke, titled "Liquid Level Sensor," describes a mechanical diaphragm type pressure regulator for controlling the pressure output to a bubble tube. The device essentially serves as a gas pressure control device required of any purge type system, but no specific means is disclosed by Luke to provide the required gas pressure or to measure the liquid depth or head by means of the pressure. In any event, the relatively simple mechanical device of the Luke U.S. Patent is incapable of determining differences in the bubble or pressure signature of the purge system while it is in operation, and thus cannot distinguish between different liquids, as can the present invention.

U.S. Pat. No. 3,987,675 issued on Oct. 26, 1976 to Christopher R. Harrison, titled "Pneumatic Level Sensing," describes a system for use with relatively large and deep tanks, as in ocean going tanker ships. Harrison requires a series of dip tubes which penetrate the tank, i.e. lower and upper bubble tubes and a balance tube, each of which increases the chance of leakage at the point of penetration. The present system requires only a single point of penetration into a closed tank. Moreover, the Harrison system requires a relatively high pressure head due to the depth of the liquid in such large tanks, and cannot make use of the relatively small pressure pump of the present invention, with its extremely high accuracy and resolution. Also, while Harrison describes a means of determining the density of the fluid in the tank by means of the difference in pressure in the down tubes, his system only works when the tank is completely full, i.e. the higher tube detects the presence of liquid to indicate the level of the liquid in the tank. Otherwise, the Harrison system cannot simultaneously determine both the level and the density of the liquid in the tank. The present invention provides a means of simultaneously determining both the pressure head or depth of the liquid in the tank, as well as the properties of the liquid at the lower end of the bubble tube by means of the bubble signature provided.

U.S. Pat. No. 4,297,081 issued on Oct. 27, 1981 to William A. Irvin, titled "Liquid Level Control System," describes a purge type system using a multiple electrical contact mercury manometer type switch. The pneumatic pump for the bubble tube is also connected in parallel to the mercury manometer, with higher pressures due to greater liquid depth resulting in higher mercury levels in the manometer. The manometer contains only a finite number of switches therein, and thus the device cannot provide indications of infinitesimally small increments, as can the present depth indicator system. Moreover, Irvin does not disclose any means of using a small and highly accurate pneumatic pump to operate his system, and to provide distinctive bubble signatures which may be resolved to determine the type of liquid disposed at the outlet of the bubble tube, as provided by the present invention.

U.S. Pat. No. 4,984,451 issued on Jan. 15, 1991 to Don J. Wilen et al., titled "Method For Determining Physical Properties Of Liquids," describes a system in which two dip tubes and a temperature probe are inserted into a container of liquid and used to determine the density or specific gravity of the liquid. The system operates using the same general principle as that described in the Harrison '675 U.S. Patent described further above, but on a much smaller scale and with greater precision. The Wilen et al. apparatus includes means to stop the gas flow in order to stabilize the pneumatic pressure upon release of gas bubbles from the lower ends of the two dip tubes, in order to allow the pressures to stabilize to provide an extremely accurate reading. By knowing the precise difference in height of the ends of the two dip tubes, the specific gravity of the liquid may be calculated with extreme accuracy. However, Wilen et al. teach away from the use of the bubble signature produced by continuous flow from the dip tube, to provide additional information. Wilen et al. treat this continuous variation in pressure as "noise" (column 1, line 49). The present invention analyzes this pressure variation during continuous flow to provide a "bubble signature," which is used to determine various characteristics, and thus the liquid type, at the lower end of the dip tube.

U.S. Pat. No. 5,059,954 issued on Oct. 22, 1991 to Paul M. Beldham et al., titled "Liquid Level Sensing System," describes a bubble tube or purge type system having intermittent operation and a timer delay in the system. When pressure falls below a predetermined level, the pneumatic pump is actuated to raise the pressure. The timer delay is also actuated. If pressure increases before the time delay period expires, this indicates that there is a leak in the pneumatic system, rather than the cause of the low pressure being a low liquid level. Otherwise, an alarm is actuated to indicate a low liquid level and the need to replenish the liquid quantity. The Beldham et al. system discloses only an open container or tank configuration, with no concentric vent system for use with closed containers, as provided in at least one embodiment of the present invention. Moreover, Beldham et al. do not disclose any means of analyzing the bubble signature from their system to determine the physical characteristics of the liquid at the lower end of the dip tube.

U.S. Pat. No. 5,163,324 issued on Nov. 17, 1992 to Glen A. Stewart, titled "Bubbler Liquid Level Sensing System," describes a system similar to that of the Harrison '675 U.S. Patent described further above, in that Stewart provides a high and a low dip tube in a closed tank. However, Stewart connects the two tubes to two separate valves and thence to a single transducer. Stewart also provides for venting the fuel vapors to the atmosphere from the transducer lines, in order to reduce the chance of damage to the transducer due to fuel vapors. The Stewart system is thus not usable in automobiles sold in the United States, as fuel vapors must be contained in such vehicles due to emissions laws. The present invention avoids any such venting of vapors to the atmosphere, and preferably provides for the upper and lower tubes to be concentric in the tank with only a single entry point in order to reduce the chance of leakage in the tank.

U.S. Pat. No. 5,953,954 issued on Sep. 21, 1999 to François Drain et al., titled "Installation And Method For Determining The Level And Density Of A Liquid In A Tank, Using A Single Immersed Bubble Probe," describes a purge type system in which the lower portion of the single tube has a larger diameter than the upper portion. Pressure is periodically reduced to zero relative to ambient tank pressure, allowing the liquid to rise within the tube to the level within the remainder of the tank. When pressure is applied to the tube, the pressure rise within the relatively smaller diameter portion of the tube is relatively rapid, and rises more slowly as the liquid is forced from the larger diameter lower portion of the tube. Knowing the height of the larger diameter portion of the tube (as well as the height of the mouth of the tube from the bottom of the tank), both the density and pressure head of the liquid may be calculated. Drain also discloses means for detecting contamination buildup within the tube, or around its mouth, by means of the uneven pressure rise as the tube is filled with air. However, he does not describe any means for detecting and measuring the bubble signature as the bubble(s) is/are released from the bottom of the tube, and correlating such signatures with the properties of the liquid at the lower end of the tube to determine the type of liquid at the mouth of the tube, as is done with the present invention.

U.S. Pat. No. 6,510,736 issued on Jan. 28, 2003 to William J. Van Ee, titled "Liquid Depth Sensing System," describes various embodiments of a purge type pneumatic depth sensing system and electrical circuitry therefor. Each of the embodiments includes separate purge or bubble tubes and vent tubes, with closed tank embodiments including a third tube for drawing gas from the tank for recirculation in a closed system. The present inventor is also the inventor of the devices of the '736 U.S. Patent. The present invention improves upon this system by providing concentric bubble and vent tubes in a single passage through the top of the tank, thereby reducing the chance of leakage. Moreover, the present system may include temperature probes to provide some of the information required to determine the type of liquid at the outlet of the bubble tube, in accordance with the viscosity and surface tension of the liquid according to the bubble signature developed. The present system also differs from the Van Ee '736 U.S. Patent in that the present system utilizes a piezoelectric pump, rather than requiring a separate motor or solenoid to drive the pump, as in the '736 U.S. Patent disclosure.

U.S. Pat. No. 6,513,376 issued on Feb. 4, 2003 to Zachary A. Prather et al., titled "Liquid Level Height Measurement System," describes a purge or bubble tube system for determining the depth of a liquid in a container, which also uses the gas which is passed through the bubble tube to carry titanium vapor for depositing upon integrated circuit boards. The system includes a series of pressurized gas containers which may be selected to supply different gases as desired. As the containers are pressurized, no pump is required in the Prather et al. system. Prather et al. do not disclose any means for measuring the minute pressure changes as gas bubbles pass from the end of the tube, and using these pressure changes to determine the type of liquid disposed at the outlet end of the tube, as provided by the present invention.

U.S. Pat. No. 6,539,796 issued on Apr. 1, 2003 to Yoshikatsu Shirai et al., titled "Liquid Level Sensor, Ampoule, And Liquid Amount Detection Method," describes a system which primary purpose is to entrain vapors from a closed tank and deposit the vapors on integrated chips to form microelectronic circuitry. The Shirai et al. system uses compressed helium as the gas, with the helium also being used in a purge tube liquid quantity measuring system, similar to the system of the Prather '376 U.S. Patent discussed immediately above. Shirai et al. have no motivation to detect foreign liquids in their system, as the system is completely closed with no possibility of contaminants entering the system.

U.S. Pat. No. 6,647,781 issued on Nov. 18, 2003 to Tyan Khak Su, titled "Bubble Water Depth Measuring Method And System Thereof," describes a system including a series of temperature compensated manometers along with a purge or bubble tube. The Su system is of relatively large scale and is adapted for measuring the depth of a relatively deep body of water, such as a lake. Su requires the temperature compensated manometers to correct for the different temperatures often found at different depths in relatively deep bodies of water. As the Su device is adapted for deep bodies of water, a relatively high pressure air pump is required to produce the pressures required to at least slightly exceed the pressures a the bottom of the body of water. A piezoelectric pump, as used in the present invention, is insufficient for use with the Su device.

Japanese Patent Publication No. 59-73,732 published on Apr. 26, 1984, titled "Purge Type Liquid Level Gauge," describes (according to the drawings an English abstract) a purge type depth indication system including periodic high pressure purges of the dip tube to flush any buildup from the tip of the tube. This system teaches away from the present system, as the system must use a relatively high pressure pump in order to provide the required pressure for flushing the tube. The small, low pressure piezoelectric pump used with the system of the present invention is not suited for use with the Hirayama device. Moreover, the patent does not disclose any means to analyze the bubble signature of his system, in order to determine the properties of the liquid at the lower end of the tube.

Japanese Patent Publication No. 60-88,324 published on May 18, 1985, titled "Purge Type Level Gauge," describes (according to the drawings and English abstract) an insert placed in the outlet end of the tube, to prevent droplet backsplash up the tube when a bubble is released. This prevents condensate buildup and corresponding restriction of the end of the bubble tube. The patent does not disclose any specific type of pneumatic pump, nor any means of analyzing the bubble signature to determine the properties of the liquid at the outlet end of the tube, as provided by the present system.

Japanese Patent Publication No. 60-102,524 published on Jun. 6, 1985, titled "Liquid-Level Measuring Apparatus," describes (according to the drawings and English abstract) a system which detects leaks in the pneumatic components by means of a frequency detector. The system correlates the bubble rate with the frequency of the alternating signal generated by the bubble stream. The system utilizes a series of separate tubes and lines into the tank, rather than a single entry point with concentric lines, as in the present invention. Moreover, no disclosure is made of analyzing the bubble signature to determine the type of liquid at the outlet end of the tube, as provided by the present invention. The system considers only the overall pulse frequency of the bubbles to detect leaks in the system, with no disclosure being apparent as to the recognition of how the shape of the pulse corresponds to the viscosity and surface tension of the liquid at the lower end of the tube, as recognized by the present invention.

Japanese Patent Publication No. 63-191,026 published on Aug. 8, 1988, titled "Purge Type Liquid Level Indicator," describes (according to the drawings and English abstract) a system for detecting condensate buildup in the output end of the bubble tube of such an apparatus. The apparatus of the '026 Japanese Patent Publication utilizes a microphone at the outlet end of the bubble tube. The sound is transformed to an electrical signal and compared to a reference signal. If the microphone signal varies beyond a predetermined level from the reference signal, an alarm is actuated to indicate the need to clean the tube. The present invention utilizes a completely different principle of signal detection and analysis for a different purpose. The present invention considers the electrical signal produced as pressure changes during the bubble release cycle, and considers the actions of the properties of various liquids upon the bubble release and resulting electrical signal to determine the type of liquid disposed at the outlet end of the tube, i.e. at the bubble release point. The '026 system does not anticipate such a possibility in any of his patent publications.

Japanese Patent Publication No. 1-74,420 published on Mar. 20, 1989, titled "Liquid Level Measuring Instrument," describes (according to the drawings and English abstract) a system closely related to the system of the '796 U.S. Patent to Shirai et al., in that it describes a single pressurized gas cylinder connected to a series of purge tubes in a series of separate tanks. No pump means is disclosed, as none is necessary due to the pressurized gas source.

German Patent Publication No. 19,826,487 published on Dec. 16, 1999, titled "Filling Level Measuring System For Measuring Level Position Of Liquid In Container According To Hydrostatic Principle With Pipeline Immersed In Liquid Which By Means Of Pump," describes (according to the drawings and English abstract) the computerized analysis of the pressure curve of the bubble stream in a purge type depth indicating system. The system averages out the pressure variations of the individual bubble pulses, and compares the pressure to a predetermined pressure to indicate when the container has been filled. The Spindler system is more closely related to the Wilen et al. '451 U.S. Patent with its averaging of the bubble signature, than it is to the present invention with its analysis of the individual pressure variations of the bubble release in order to determine the properties of the liquid at the lower end of the dip tube.

Finally, a web page published by SITA Messtechnik Gmbh, at least as of Mar. 16, 2004, describes the principles of the phenomenon of surface tension, and a series of instruments and programs for measuring the surface tension of a liquid by measuring the duration of the bubbles produced in a purge tube apparatus. The various instruments and programs are primarily directed to analyzing the concentration of surfactants (detergents) in water, for use in the commercial laundry industry. However, these instruments and surface tension measurement systems teach away from the present invention, as they are only directed to the results of the addition of a single substance, i.e. a detergent or surfactant, to water. No consideration is shown for the effects of other types of liquids on the bubble frequency, nor is the effect of different liquid viscosities considered. In contrast, the present invention considers the overall bubble signature, i.e. pressure changes and duration, to arrive at a signal which is unique for different liquids. In this manner, the contamination of one liquid in a container by another liquid disposed at the bottom of the container can be detected using the present system.

None of the above inventions and patents, taken either singly or in combination, is seen to describe the instant invention as claimed. Thus a liquid depth sensing system with liquid identification capability solving the aforementioned problems is desired.

SUMMARY OF THE INVENTION

The present liquid depth sensing system with liquid identification capability comprises various embodiments of a purge or bubble tube type depth measuring system which is also capable of determining the type of liquid disposed at the lower end of the dip tube of the system. The present inventor has found that by providing an extremely consistent bubble stream, and by accurately measuring the pressure pulses as the bubbles are emitted from the end of the bubble tube, that it is possible to relate these "bubble signatures" to the type of liquid at the outlet end of the bubble tube.

This discovery, and the present invention resulting from the discovery, has far reaching applications. One of the most critical fields to which the present invention may be applied, is aviation. Contamination of aviation fuel with water, or with other types of incompatible fuels is a well known problem with potentially disastrous results. The present invention is capable of not only determining the depth of the fuel in a tank, but also of detecting any water or other incompatible liquid at the lower end of the dip tube in the tank. The present invention may also be applied to the motor vehicle field, where it may be adjusted to provide indications and/or automatic adjustments to the vehicle engine for different grades of diesel or spark ignition engine fuel, depending upon the vehicle and system. It is also readily adaptable to installation in fuel oil tanks and similar systems, where it can perform the same functions as noted above.

The present liquid depth measuring system with its liquid identification capability uses a very small piezoelectric diaphragm pump to supply the air or gas flow through the dip tube of the system. This provides several benefits in the reduction of componentry and cost in comparison to earlier systems of the related art. By sizing the pump and adjusting its actuation pulse rate properly, the pump may be made to produce a very consistent and uniform bubble pattern. This provides the benefits of eliminating the need for a differential pressure transducer, constant flow restrictor and its accompanying filter, ambient pressure sense line, and the corresponding pneumatic and electrical connections.

The present system includes a pressure sensor which transforms the air stream pressure of the dip tube to an electric signal, with the voltage varying according to the pressure variation. The present system is capable of detecting minute variations in pressure during the cycle of a single bubble forming in the end of the tube and exiting the tube. These minute pressure variations are transformed to an electrical signal of correspondingly varying voltage. As different liquids have different properties of viscosity, surface tension, specific gravity, etc., the present liquid identification system can recognize these different liquids in accordance with their different bubble signatures, which results from the varying surface tensions and viscosities of the different liquids.

The present system has many far reaching advantages, as noted further above. The bubble recognition signal may be used to communicate directly with an engine control unit (ECU) in a motor vehicle, to adjust the timing, limit throttle opening, and/or adjust engine operation in some other manner, in response to signals identifying different grades of fuels, all without requiring input from the vehicle operator. Annunciator warnings of some sort could be provided to alert the operator of other contaminants in the fuel system, e.g. water. The present system may be employed in diesel vehicles as well, for differentiating between different grades of diesel fuel and adjusting engine operation accordingly. Many other benefits may be provided by the present system, in addition to those briefly touched upon above.

These and other features of the present invention will become apparent upon consideration of the following specification and drawings.

BRIEF DESCRIPTION OF THE DRAWINGS

FIG. 2 is a schematic side elevation view of another embodiment of the present invention installed in an open vented tank, as in a fuel oil tank or the like.

FIGS. 5A, 5B and 5C are detailed elevation views of the bubble emission cycle of the lower end of the dip tube of the present liquid depth and identification invention.

Similar reference characters denote corresponding features consistently throughout the attached drawings.

DETAILED DESCRIPTION OF THE PREFERRED EMBODIMENTS

The present invention comprises embodiments of a purge tube type depth indicator system, including at least one embodiment which determines both the depth and the type of liquid disposed at the dip tube outlet. This is accomplished by a precision pneumatic pump and means for determining the "bubble signature" emitted from the tube, which varies according to the liquid type.

Figure 1:
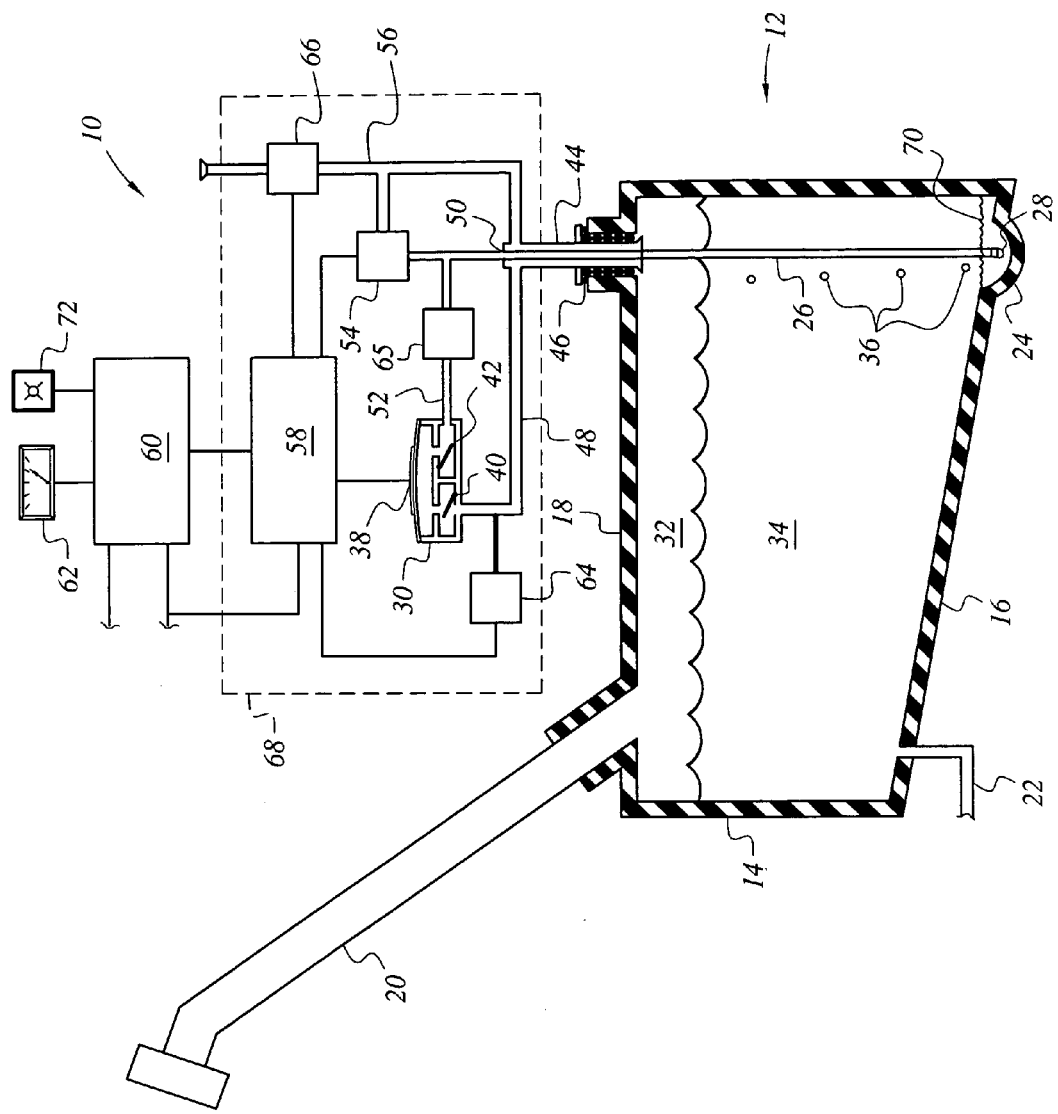
FIG. 1 is a schematic side elevation view of a liquid depth sensing system with liquid identification capability installed in a closed tank, in accordance with the present invention.

FIG. 1 provides a schematic side elevation view of a first embodiment of the present invention, wherein the liquid depth sensing and liquid identification apparatus 10 is installed with a closed liquid container 12 having a peripheral wall 14, floor 16, and closed top 18. The container 12 conventionally includes a filler pipe or neck 20 and an outlet line 22, as is typical in fuel tanks of various types. The outlet line 22 often extends from a higher point in the tank floor 16, in order to avoid picking up contaminants or anomalous liquids (e.g., water) which settle to the bottom of the tank 12. A sump 24 may be provided at the low point of the tank 12, to capture such contaminants.

The present system 10 is based upon the purge tube type system, wherein a gas delivery dip tube 26 extends into the tank 12. The tube 26 has an open lower end 28 slightly above the tank floor 16, with a pneumatic gas supply pump 30 forcing air (or other gas, e.g. air and vapor 32 from the interior of the tank 12) through the tube 26. The liquid 34 in the tank 12 creates a pressure head at the lower end 28 of the tube 26, with the pressure varying according to the depth of the liquid 34. The system 10 provides sufficient gas pressure through the tube 26 to force the liquid from the interior of the tube 26, and to bubble from the lower end 28 of the tube 26. When the gas departs the open lower end 28 of the tube 26 by forming gas bubbles 36, the gas pressure in the system is equal to the pressure head at the mouth 28 of the dip tube 26. The gas pressure may be read and equated to the pressure head of the liquid 34, thereby enabling the depth of the liquid 34 in the tank 12 to be determined.

The above generally described purge or bubble tube type liquid depth indicator system is essentially conventional, and is basically the type of system upon which the system of the present inventor's '736 issued U.S. Patent is based. However, the present inventor has made numerous improvements over his earlier patented system and other systems of the related art. For example, the bubble tube systems of the related art and of the present inventor's issued U.S. Patent universally provide some means of dampening the pressure pulses in order to provide an average pressure, and therefore liquid depth, over some period of time. This period is generally relatively short, but still exceeds the duration of one cycle of bubble emission from the outlet end 28 of the dip tube 26.

However, the present inventor has found that by using a specialized, miniature pneumatic diaphragm pump, e.g. pump 30 of FIG. 1, much finer resolution of the pressure changes over a given time period may be achieved. This fine resolution of the pressure variations over each bubble emission cycle provides additional information heretofore considered to be "noise" by other patentees, cf. Wilen et al. '451 U.S. Patent discussed further above. In fact, by using a miniature diaphragm pump 30, and adjusting the pump 30 output to provide a consistent and uniform bubble stream 36 from the outlet end 28 of the dip tube 26, the present inventor has found that the pressure pulses in the system may be read with instrumentation providing sufficiently fine resolution, and that these pulses can provide considerable information about the liquid(s) in the tank 12.

The pump 30 is preferably a piezoelectric device, i.e. using a dielectric crystal 38 to develop mechanical force when electrical energy is applied thereto. Other means of actuating the present pump, e.g. a small voice-type coil, etc., may be used as desired. The critical point is that the electrically actuated mechanical means for operating the pump 30 be integrally disposed with the pump 30, generally as shown in the schematic view of FIG. 1. This arrangement has been found to provide extremely precise control of the pneumatic output of the pump 30, to provide the extremely consistent bubble stream 36 which is desired to provide the desired pressure cycle resolution.

The pump 30 operates by drawing gas or vapor through its inlet valve 40 when the piezo (or other) diaphragm 38 is raised, and expelling the gas through the outlet valve 42 when the diaphragm 38 is lowered. The gas 32 passes upwardly through a vent tube 44, which is preferably disposed concentrically about the dip tube 26 to extend into the tank or container 12 through a common peripherally sealed passage 46 in order to avoid additional passages and potential leakage points from the tank 12. The vent tube 44 communicates pneumatically with the inlet valve 40 side of the pump 30 by a pump inlet line or tube 48. The upper end 50 of the vent tube 44 is sealed about the upper portion of the dip tube 26. The outlet valve 42 side of the pump communicates pneumatically with the dip or purge tube 26 by means of a pump outlet line or tube 52, to complete the basic pneumatic circuit. It will be noted that the above described system is closed, with vapor unable to escape to the atmosphere.

The above described system 10 provides a determination of the liquid (fuel, etc.) level in the container or tank 12 by means of a differential pressure sensor 54, pneumatically disposed between the dip tube 26 and the vent tube 44 by means of a branch 56 extending therefrom. Gas or vapor cannot pass through the differential pressure sensor 54; it serves only to measure the pressure difference between the pressure in the dip tube 26 and its supply line 52, and ambient pressure on the liquid in the tank, i.e. pressure of the air, gas, and/or vapor 32 within the closed system, or ambient atmosphere in an open system.

The differential pressure sensor 54 communicates electrically with a controller 58, with the sensor 54 sending electrical signals corresponding to the pressure head, and therefore the depth, of the liquid in the tank 12 to the controller 58. The controller 58 communicates electrically with the pump 30, signaling the pump 30 to operate depending upon the pressure information provided by the pressure sensor 54. The controller 58 also communicates electrically with a processor 60, which converts the pressure signal from the controller 58 to a depth indication corresponding to the pressure head of the liquid 34 sensed by the differential pressure sensor 54. The liquid depth information signal is then sent to a liquid quantity gauge 62 (e.g., fuel gauge, etc.). The processor 60 may be programmed with the shape of the tank 12, to provide a precise indication of the quantity of liquid within the tank 12 regardless of the level of the liquid 34 therein.

The above described system operates using an open loop pulse control principle, rather than the closed loop operation of the present inventor's previously patented device. In the present system, the miniature diaphragm pump 30 has been specifically selected to provide the proper gas flow without any requirement for pressure regulators, flow controllers, and/or filters as required by bubble or purge tube type systems of the related art, including the present inventor's previously patented system. Rather than using such regulators and control devices to control the pneumatic output of the pump 30, the controller 58 of the present invention sends actuation pulse signals to the pump 30 at a fixed rate. This constant pump flow system works well for use in containers and tanks to which the present invention is directed, i.e. aircraft and motor vehicle fuel tanks, oil and hydraulic tanks, and other containers of similar depth. The pulse rate may be adjusted according to the specific gravity and depth range (pressure head) of the liquid being measured, but once it has been adjusted, no further readjustment is required, and thus no additional circuitry is needed.

It will be seen that such a system is open loop, i.e. it is not controlled by the varying pressure head of the liquid in the tank affecting the gas pressure in the system. The controller 58 only provides pulse signals to the pump 30 as required, and may operate continually or may be operated intermittently by means of a conventional timer chip or the like provided with or integrated with the controller 58, or by some other manual or automated switching means as desired.

The above described open loop control system has many advantages over closed loop systems of the prior art. As noted further above, the present open loop system does not require any form of pressure or flow regulators or controls. This results in the elimination of filters as well, as the only reason such filters are required in other systems is to protect the various regulators from contamination. The present open loop system is thus not only more efficient and more accurate than earlier closed loop systems, but is also more economical to manufacture due to the reduction in the number of components required.

The accuracy and consistency of the above described open loop control system and miniaturized diaphragm pump provide further advantages, as well. The miniaturized, solid state differential pressure transducer or sensor 54 provides extremely accurate pressure information, with very rapid update capability. Heretofore, such rapid response was not considered to be of any value in liquid depth measurement, as the liquid depth does not change particularly rapidly in most situations. Accordingly, in the past the rapid pressure pulses have been damped by the installation of various regulators, filters, etc. in such systems. However, the present system does not require these various components which act to smooth out the pressure pulses which may otherwise be detected by the system. While testing the present invention in various liquids, the present inventor observed that the unregulated and unfiltered signal output by the pressure transducer 54, indicated a very consistent and uniform wave form corresponding to the bubble flow.

This extremely fine resolution of the bubble wave form was noted to vary, depending upon the type of liquid disposed at the output end of the dip tube 26. The present inventor has determined that the primary factors involved in the variation of the waveform output of the differential pressure sensor or transducer 54 is due to the variation in surface tension and viscosity between different liquids. The surface tension and viscosity of a given liquid are quite consistent properties. However, they may vary to some extent according to the temperature of the liquid.

Accordingly, a temperature sensor 64 is installed along the vent tube branch 48 to the pump inlet valve 40 and senses the temperature of the vapor or gas 32 as it circulates from the upper portion of the tank or container 12, through the vent tube 44 and the pump inlet line 48 to the pneumatic pump 30. However, the vapor or gas circulates through the liquid 34 in the tank 12 as the pump 30 expels the gas 32 from the outlet end 28 of the dip tube 26. Thus, the vapor or gas 32 will have substantially the same temperature as the liquid 34. This arrangement precludes need to install another hole or passage through the tank top 18 or wall 14 for the installation of a temperature probe, while providing a reasonably accurate indication of the temperature of the liquid 34. The processor 60 may be programmed to compensate for any significant temperature differences. Detailed graphs of the wave forms or "bubble signatures" for various liquids are shown in FIGS. 4A through 4G, and discussed in detail further below.

Optionally, a suppressor or damper 65 may be installed in the outlet line 52 between the pump 30 and the upper portion of the dip tube 26 extending to the differential pressure sensor 54. The suppressor 65 serves to dampen or smooth out any extremely short term spikes or "noise" in the pressure pulses produced by the pump 30 and delivered to the differential pressure sensor 54. The wave forms or "bubble signatures" which may be produced graphically and interpreted to determine the type of liquid at the dip tube outlet, may be more easily interpreted when the relatively miniscule, extremely short term pulses are canceled by the suppressor 65. The suppressor 65 may comprise a small canister or the like operating much like a conventional sound or noise suppressing muffler or resonator, i.e. having pressure pulse absorbent material (steel wool glass fiber, etc.) therein and/or including a sinusoidal or labyrinthine flow path therethrough. It should be noted that this device 65 does not act as a regulator or filter any more so than an automotive muffler acts as a regulator or filter for automotive exhaust systems. The major portions and distinctive features of the wave forms or bubble signatures of various liquids are still readily discernible with such a suppressor 65 installed in the system, without the critical features of the wave forms being concealed by myriad small, short term "noise" spikes in the wave forms.

The above described system 10 illustrated schematically in FIG. 1 is well suited for closed systems, such as motor vehicle fuel tanks and the like where fuel vapors must be contained. Such systems generally include a vapor pressure sensing device, such as the device 66 provided with the present system 10. The vapor pressure sensor 66 does not vent fuel or other vapors or gases to the atmosphere, but rather compares the pressure of the vapor 32 in the tank vent lines 44, 48, and 56 with atmospheric pressure. This pressure is communicated electronically to the controller 58 and/or to the processor 60.

It will be noted that all electrical and electronic components, i.e. the pump 30, differential pressure sensor 54, controller 58, processor 60, quantity indicator 62, temperature sensor 64, and vapor pressure sensor 66, are disposed externally relative to the liquid container 12. All of the above components excepting the processor 60 and quantity indicator 62, may be contained in a housing 68 (shown in broken lines in FIG. 1). This arrangement precludes the possibility of any electrical arcing or sparking within the liquid container 14. Thus, the present liquid quantity indicator system with its anomalous liquid detection system, is well suited for use with combustible liquids such as automotive and aircraft fuels, oils, hydraulic fluids, etc. Moreover, by removing all such electrical components from the interior of the tank 12, exposure to potentially corrosive environments, e.g. water in a water tank, is precluded, thereby extending the life of such electrical and electronic components.

Figure 2:
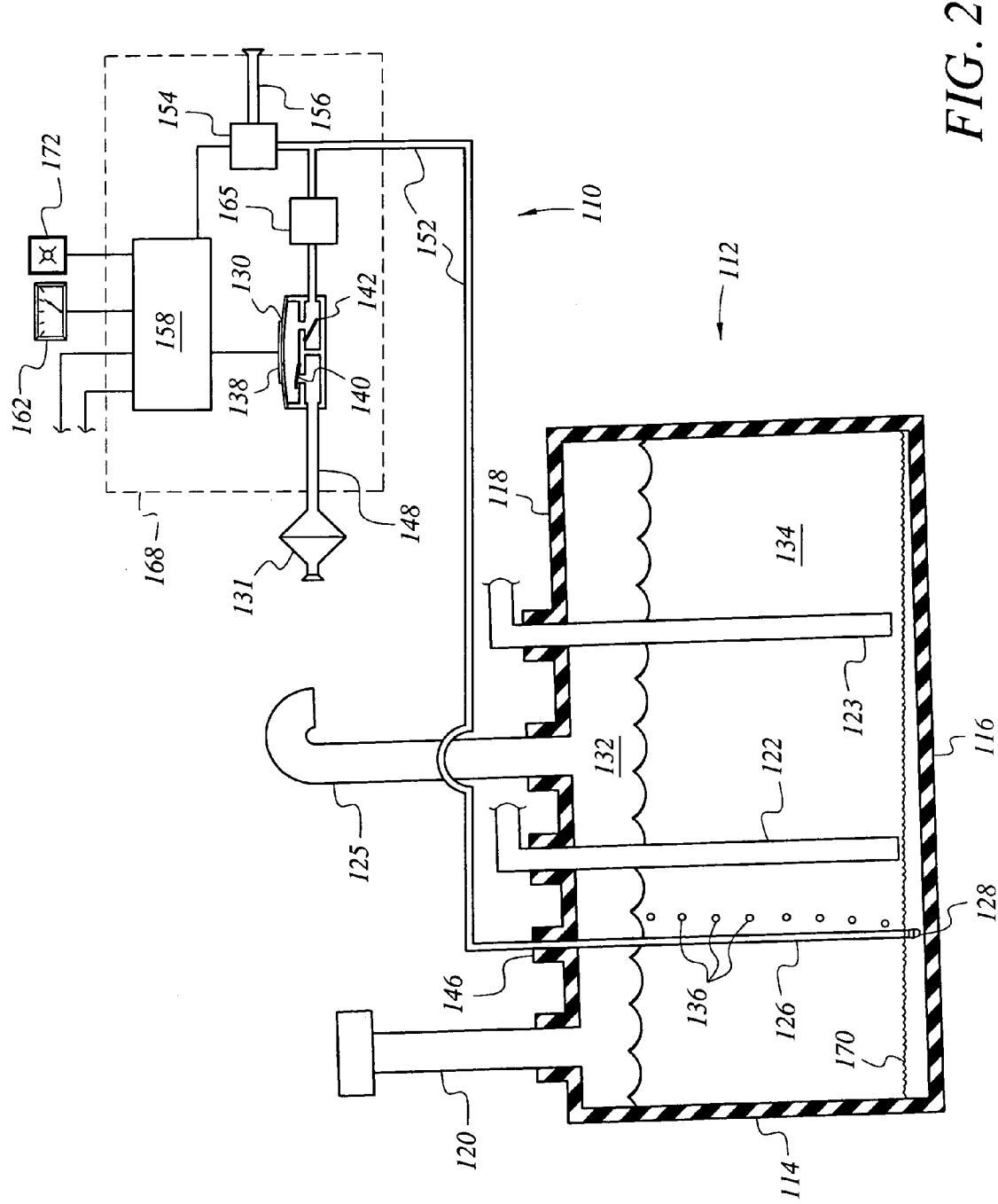

FIG. 2 provides a schematic illustration of another embodiment of the present invention, installed with a tank or container the interior of which is open to the atmosphere. Such tanks or containers are conventionally installed above or below ground for storing fuel oil and the like, as well as for other purposes. The system 110 of FIG. 2 communicates pneumatically with an open container or tank 112, with the container 112 having a peripheral wall(s) 114 and a bottom or floor 116. While the tank or container 112 also includes a top or cover 118, it is vented to the atmosphere, rather than being a closed system, as in the container 12 of FIG. 1. The tank or container 112 includes a filler neck 120 and outlet and return lines or pipes, respectively 122 and 123, as well as a vent pipe 125 which is open to the atmosphere.

The container or tank 112 includes a dip tube 126 with its open outlet end 128 spaced slightly above the floor 116 of the tank 112. Air is provided to the dip tube 126 by a pneumatic pump 130, which is preferably of the same type as the pump 30 described for the embodiment of FIG. 1. Ambient air is drawn into the pump 130 through a filtered inlet 131 and inlet line 148, and pumped through the pneumatic system to the dip tube 126 to escape from the outlet end 128, where it bubbles to the upper area of the container or tank 112 as air pocket 132. The air 132 is then free to escape the container 112 through the open vent pipe 125, where it is vented to the atmosphere rather than being confined to the tank interior, as in the embodiment of FIG. 1.

The system 110 of FIG. 2 operates much like the system 10 of FIG. 1, i.e. the pressure of the air at the bottom end 128 of the dip tube 126 is equal to the pressure head of the liquid 134 (e.g., fuel oil, etc.) in the container 112. When the air pressure in the dip tube 126 and the remainder of the pneumatic system reaches the pressure of the liquid 134 at the bottom of the dip tube 126, the air escapes from the dip tube 126 in the form of bubbles 136. Air pressure is provided by the action of the piezo or other actuator 138 of the pump 130, alternately opening and closing the inlet and outlet valves 140 and 142 of the pump 130 to pump air through the system. There is no air outlet vent tube per se in the system of FIG. 2, corresponding to the concentric vent tube 44 of FIG. 1. Rather, the air escapes the tank or container 112 through the open vent pipe 125, as noted further above.

The open tank or container 112 of FIG. 2 includes only a single pneumatic line, i.e. the dip tube 126, extending through its passage 146 in the top 118 of the tank 112. Alternatively, the dip tube 126 could be installed through the vent pipe 125, thus avoiding need for any modification to an existing conventional tank or container 112. The dip tube 126 is pneumatically connected to the pump 130 by a pump outlet line 152, which extends from the pump outlet and its valve 142 to the dip tube 126. A branch of the outlet line 152 extends from a tee to a differential pressure sensor 154, which senses the pressure difference between the inlet line 152 to the dip tube 126 and the ambient atmosphere, by means of a vent tube 156. A suppressor 165 may be installed in the pump outlet line 152 between the pump 130 and the differential pressure sensor 154 to dampen miniscule "noise spikes" which may be produced by the pump 130, generally in the same manner as the suppressor 65 installation in the system 10 shown in FIG. 1.

The differential pressure sensor 154 communicates electrically with a controller 158, which converts the pressure information received from the differential sensor 154 to a signal which is sent to a quantity gauge 162, for determining 15' the quantity of liquid 134 in the container 112. The controller 158 also communicates electrically with the pump 130, and serves to drive the pump 130 to produce the pneumatic pressure required to operate the present system 110. The circuit is open loop, as in the case of the open loop circuit of the system 10 of FIG. 1. Thus, varying pressure input signals from the differential pressure sensor 154 have no effect on the pulses delivered to the pump 130 to drive the pump. The pump drive pulses are provided in accordance with predetermined settings, and are independent of the quantity of liquid 134 in the tank or container 112.

As in the case of the apparatus of FIG. 1, the electrical and electronic apparatus of the system 110 of FIG. 2 is completely removed from the interior of the container or tank 112, with only the pneumatic portion of the device, i.e. the dip tube 126, extending into the interior of the tank 112. The advantages of keeping all electrical and electronic components and circuitry from the liquid within a container or tank are well known and noted further above in the detailed description of, the apparatus of FIG. 1. The electrical and electronic components of the apparatus 110 of FIG. 2 may be contained in a housing or shell 168 for protection and to serve as a common location for the various components, similarly to the housing 68 for the apparatus 10 of FIG. 1.

Figure 3:
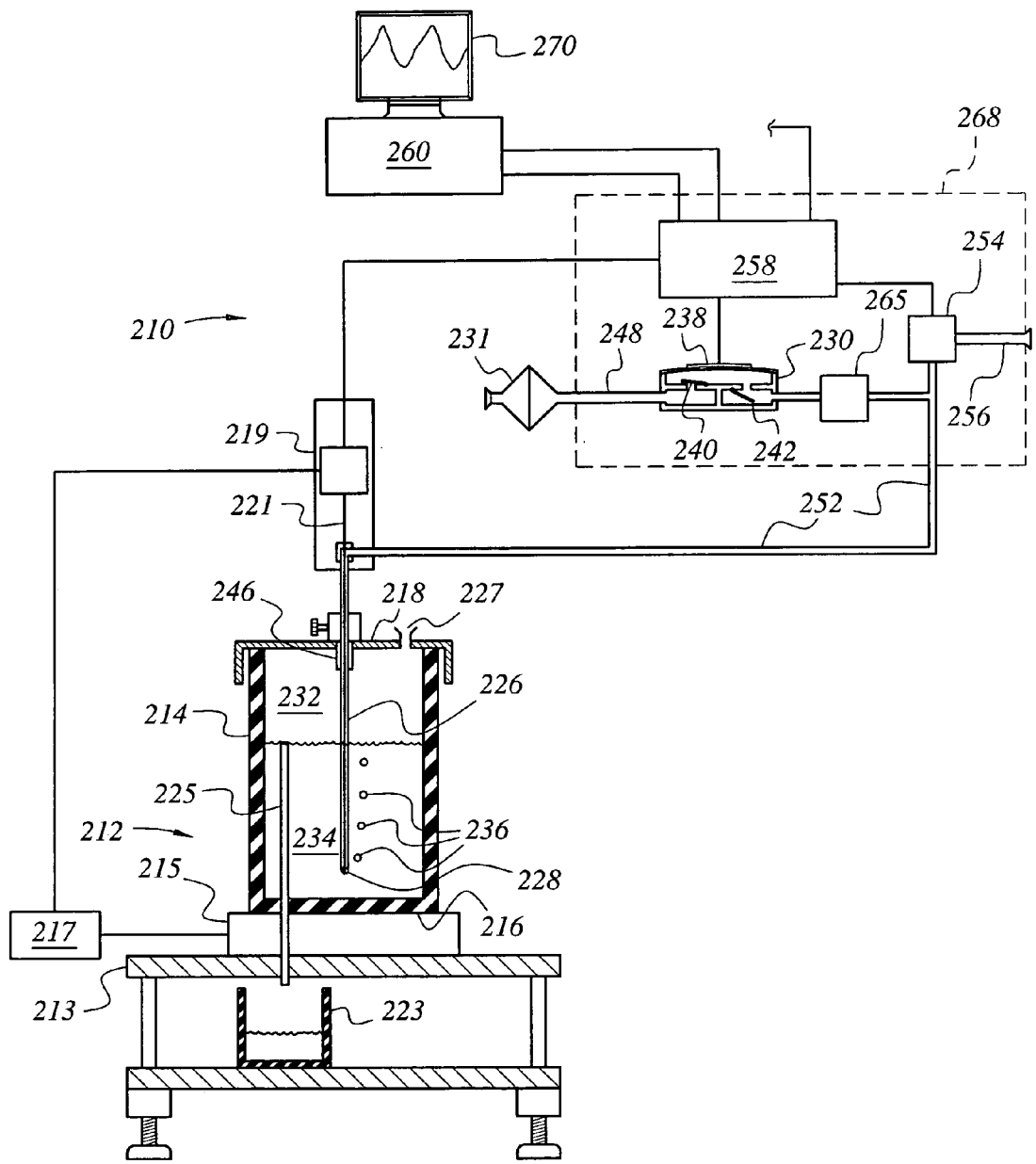
FIG. 3 is a schematic side elevation view of test apparatus for determining the bubble signature of various liquids.

FIG. 3 provides a schematic illustration of a test apparatus 210 comprising a fluid wave form standardization beaker which may be used to determine the wave form or "bubble signature" of any of a variety of different liquids. The present inventor has found that with the elimination of the regulators and filters provided by the miniaturized diaphragm pump used with the devices of the present invention, that the different wave forms or "bubble signatures" may be detected by an oscilloscope or other suitable means. These different bubble signatures correspond to different properties of different liquids at the outlet end of the dip tube, and the resulting pressure pulses as the bubbles are emitted individually from the lower end of the dip tube. Detailed drawings of the phases of bubble emission are provided in FIGS. 5A through 5C, while a series of wave forms or bubble signatures for different liquids is shown in FIGS. 4A through 4G and discussed further below.

The various identical or equivalent components of the apparatus 210 of FIG. 3 are indicated by reference numerals having identical second and third digits to those components of FIGS. 1 and 2. In FIG. 3, the apparatus or system 210 is shown being used as a test apparatus for determining the wave form characteristics or "bubble signatures" of various liquids. An open cup or container 212 having a peripheral wall 214 and bottom or floor 216 is placed upon a test stand 213, with the apparatus 210 of the present invention disposed thereabove. The container 212 may include a top or cover 218, but the top is preferably vented to ambient air and primarily serves as an anchor point for the dip tube.

The test stand 213 preferably includes a temperature control device 215 beneath the test container 212 and a controller 217 for the temperature control device, in order to maintain the liquid within the container 212 at a constant temperature. The controller 217 may in turn be controlled by a temperature sensor 219, which communicates with the liquid by means of a temperature probe 221 which extends concentrically through the dip tube 226. An overflow container 223 may be located below the container 212 as well, with an overflow tube 225 extending from the upper level of the liquid to the overflow container 223 in order to maintain the liquid in the test container 212 at a constant level.

The test container 212 includes a dip tube 226 with its open outlet end 228 spaced slightly above the floor 216 of the container 212. The exact spacing of the lower end 228' of the dip tube 226 in the container 212 is not so critical here as it is in applications where the system is used to determine the total depth of the liquid in the container or tank, as in the cases of the devices of FIGS. 1 and 2. Air is provided to the dip tube 226 by a pneumatic pump 230, which is preferably of the same type as the pump 30 described for the embodiment of FIG. 1. Ambient air is drawn into the pump 230 through a filtered inlet 231 and inlet line 248, and pumped through the pneumatic system to the dip tube 226 to escape from the outlet end 228, where it bubbles to the upper area of the test container 212 as air pocket 232. The air 232 is then free to escape the container 212 through the open vent 227, where it is vented to the atmosphere rather than confined to the container interior, as in the system of FIG. 1.

The system 210 of FIG. 3 operates much like the system 10 of FIG. 1, i.e. the pressure of the air at the bottom end 228 of the dip tube 226 is equal to the pressure head of the liquid 234 (e.g., water, fuel, hydraulic fluid alcohol, etc.) in the container 212. When the air pressure in the dip tube 226 and the remainder of the pneumatic system reaches the pressure of the liquid 234 at the bottom of the dip tube 226, the air escapes from the dip tube 226 in the form of bubbles 236. Air pressure is provided by the action of the piezo or other actuator 238 of the pump 230, alternately opening and closing the inlet and outlet valves 240 and 242 of the pump 230 to pump air through the system. There is no air outlet vent tube per se in the system of FIG. 3, corresponding to the concentric vent tube 44 of FIG. 1. Rather, the air escapes the test container 212 through the open vent 227, as noted further above.

The open container 212 of FIG. 3 includes only a single pneumatic line, i.e. the dip tube 226, extending through its passage 246 in the top 218 of the container 212. Alternatively, the dip tube 226 could be clamped or otherwise secured to the edge of the container 212, thus avoiding need for a top for the container 212. The dip tube 226 is pneumatically connected to the pump 230 by a pump outlet line 252, which extends from the pump outlet and its valve 242 to the dip tube 226. A branch of the outlet line 252 extends from a tee to a differential pressure sensor 254, which senses the pressure difference between the inlet line 252 to the dip tube 226 and the ambient atmosphere by means of a vent tube 256. As in the embodiments of FIGS. 1 and 2, a suppressor 265 may be installed in the pump outlet line 252 between the pump 230 and the differential pressure sensor 254, to dampen miniscule pressure spikes produced by the pump.

The differential pressure sensor 254 communicates electrically with a controller 258, which converts the pressure information received from the differential sensor 254 to a signal which is sent to a computer 260 for further processing of the signal for liquid identification, as described further below. The controller 258 also communicates electrically with the temperature sensor 219 to provide liquid temperature information to the computer 260, as well as communicating with the pump 230 to drive the pump 230 to produce the pneumatic pressure required to operate the present system 210. The circuit is open loop, as in the case of the open loop circuits of the systems 10 of FIGS. 1 and 110 of FIG. 2. Thus, varying pressure input signals from the differential pressure sensor 254 have no effect on the pulses delivered to the pump 230 to drive the pump.

The electrical and electronic apparatus of the system 210 of FIG. 3 is completely removed from the interior of the container 212, with only the pneumatic and temperature probe portions of the device, i.e. the dip tube 226 and temperature probe 221, extending into the interior of the container 212. The advantages of keeping all electrical and electronic components and circuitry from the liquid within a container are well known and noted further above in the detailed description of the apparatus of FIG. 1. The electrical and electronic components of the apparatus 210 of FIG. 3 may be contained in a housing or shell 268 for protection and to serve as a common location for the various components, similarly to the housings 68 and 168 for the devices 10 and 110 respectively of FIGS. 1 and 2.

FIGS. 4A through 4G illustrate a series of different wave forms or "bubble signatures" of bubble emissions through a series of different liquids, while FIGS. 5A through 5C provide detailed illustrations of a series of three steps in the process of bubble emission from the end of a dip tube, corresponding to the wave forms or bubble signatures of FIGS. 4A through 4G. The series of wave forms of FIGS. 4A through 4G are generated by measuring the minute variations in pressure detected by the differential pressure sensor 254 as the bubbles reach and depart the outlet end of the dip tube. The bubble signature traces or wave forms may be viewed on the computer monitor 270 of the apparatus 210 of FIG. 3, and/or printed out in graph form, similar to the wave forms or bubble signatures shown in FIGS. 4A through 4G.

Figure 4A:
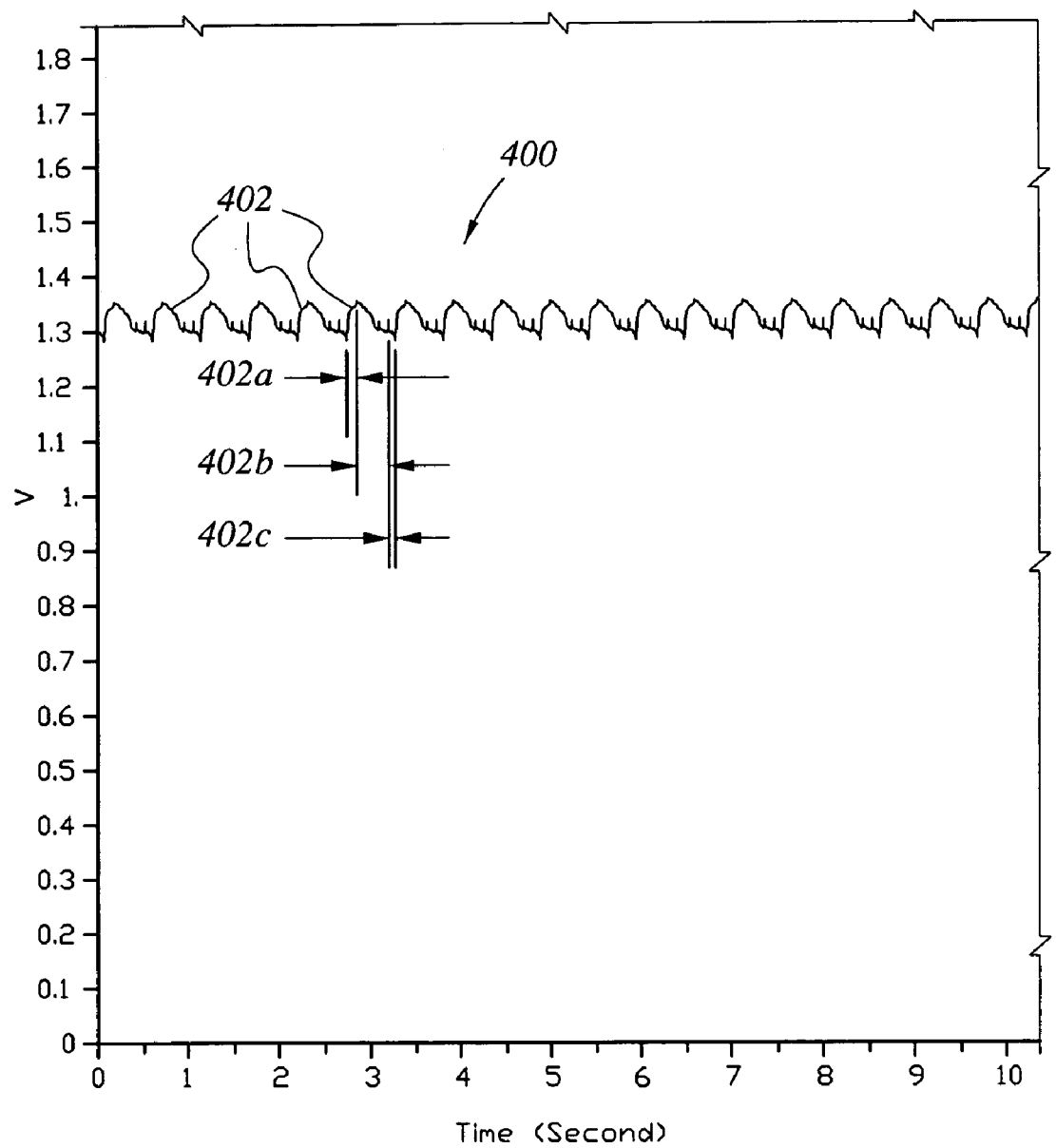
FIGS. 4A, 4B, 4C, 4D, 4E, 4F, and 4G are charts respectively illustrating the pressure variation over time, i.e. the bubble signatures, of 87, 89, and 93 octane gasolines, E-85 fuel, No. 1 and No. 2 diesel fuels, and water, using the present invention.
Figure 4B:
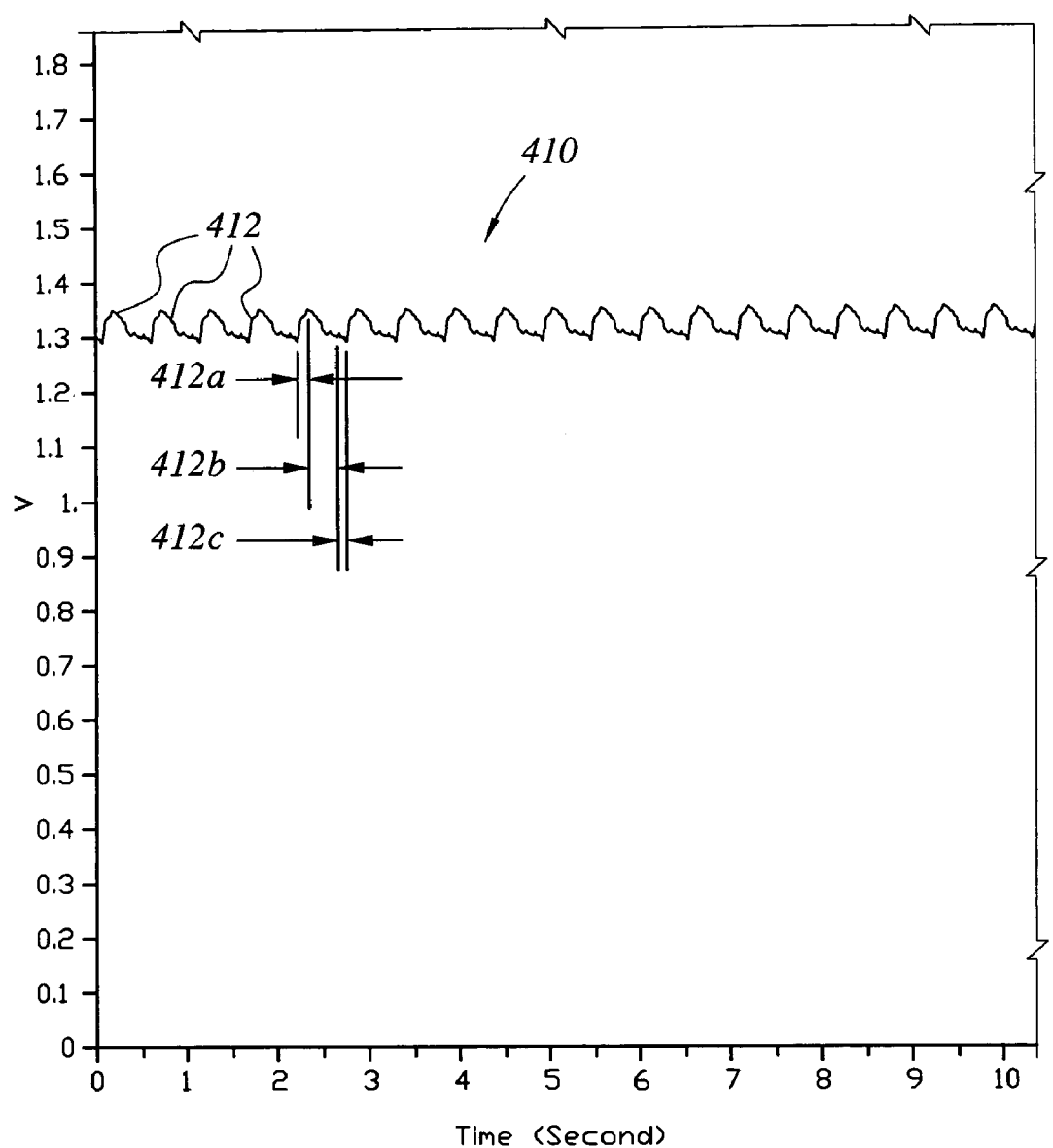
Figure 4C:
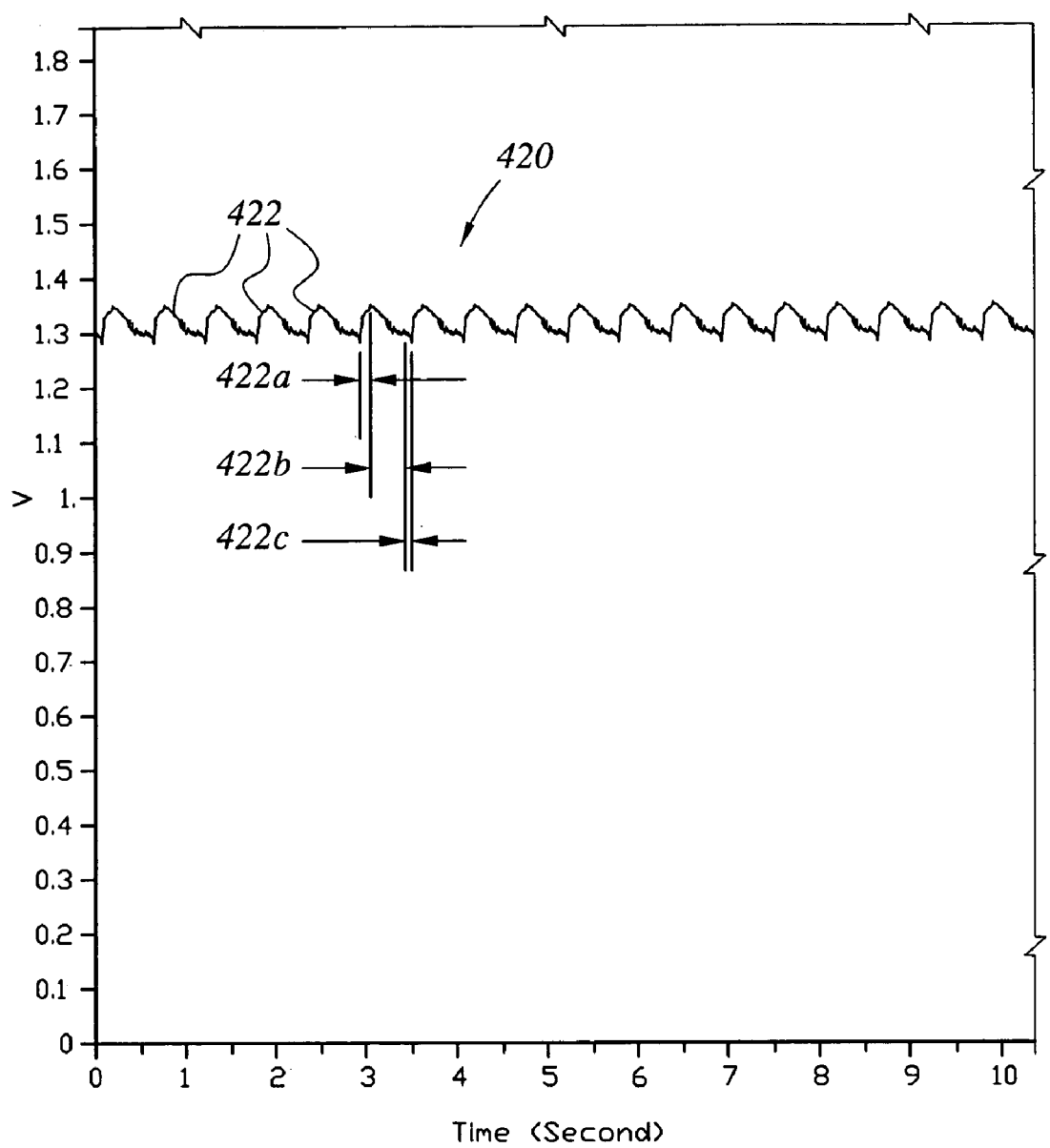
Figure 4D:
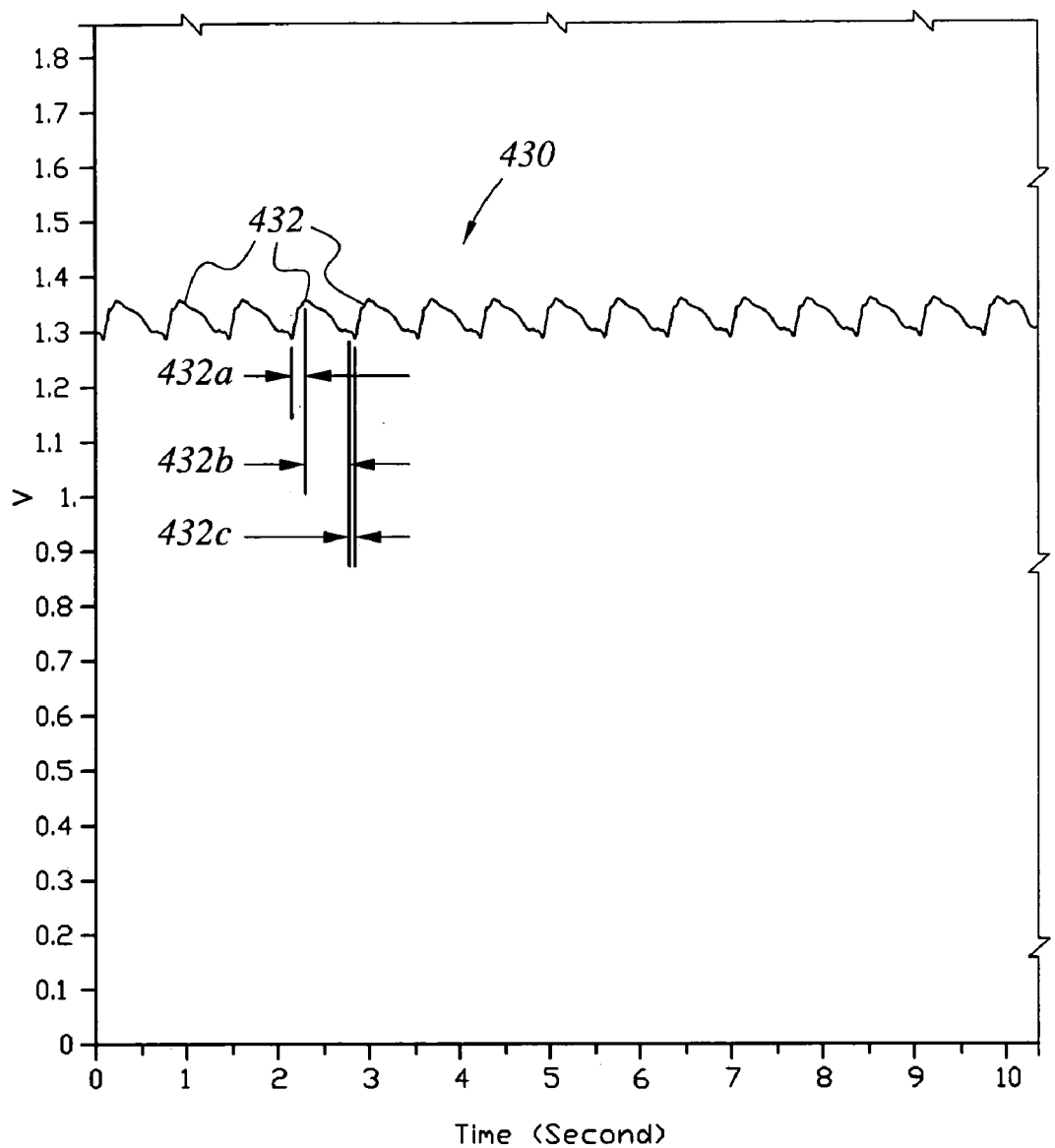
Figure 4E:
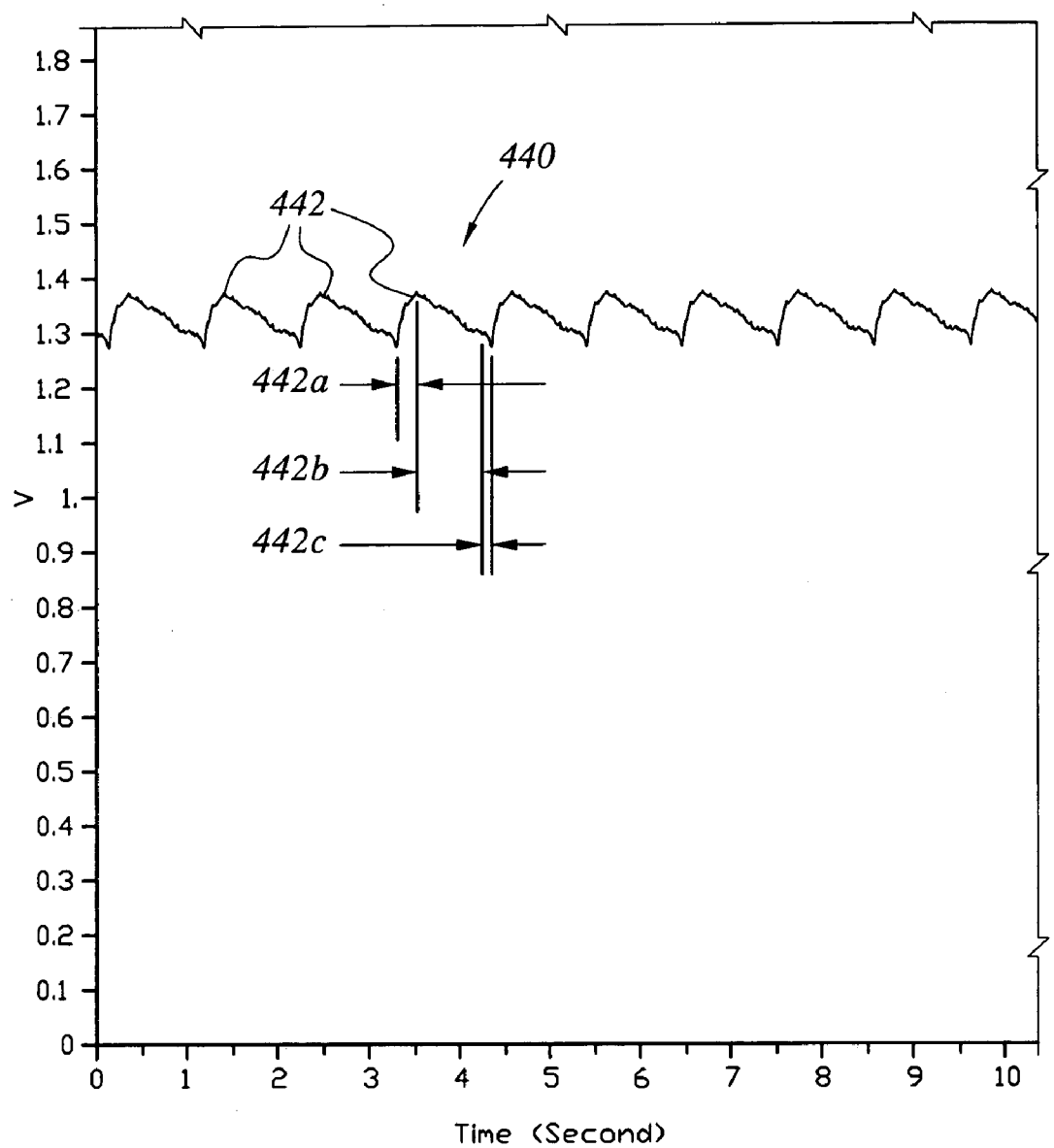
Figure 4F:
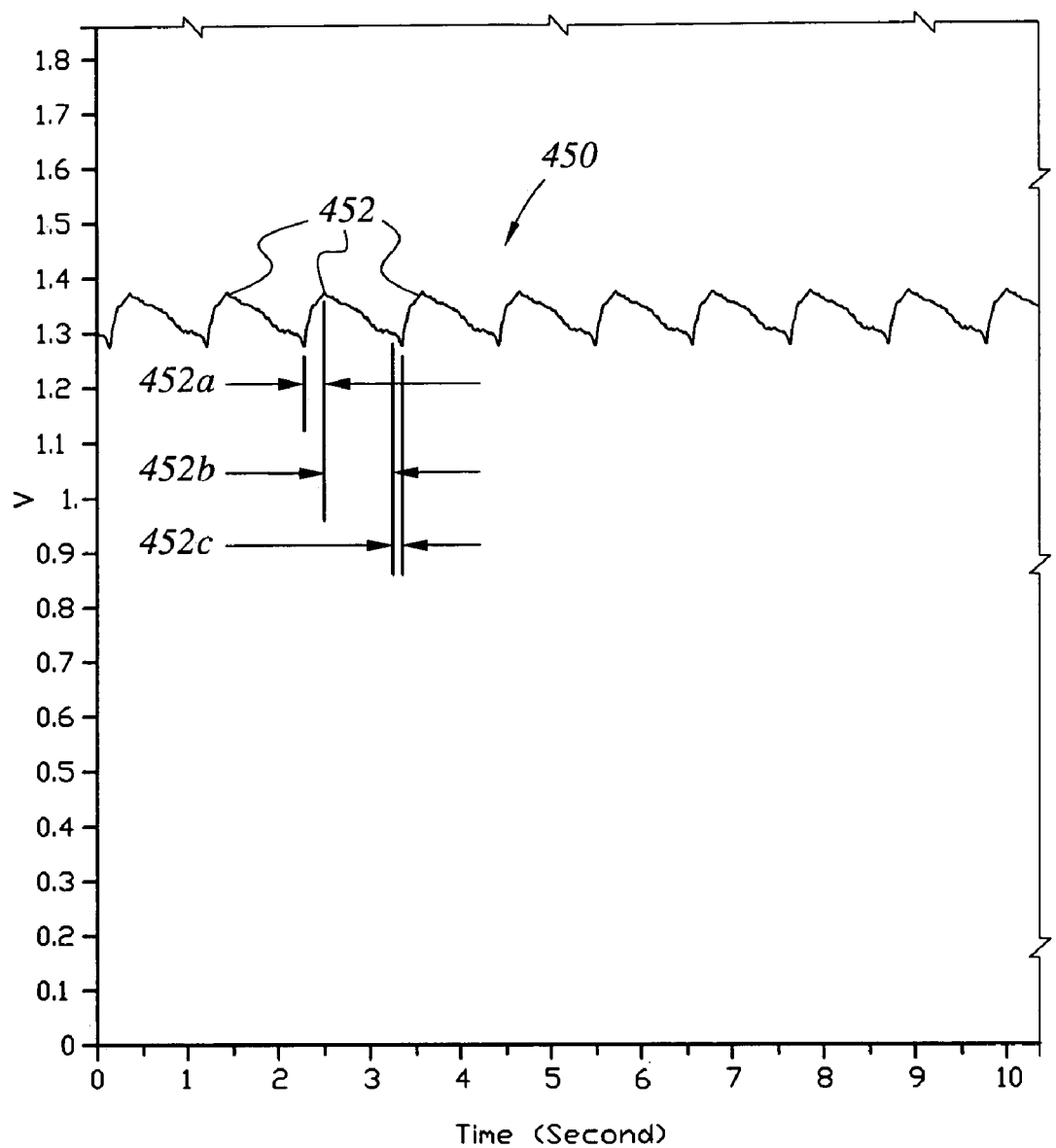
Figure 4G:
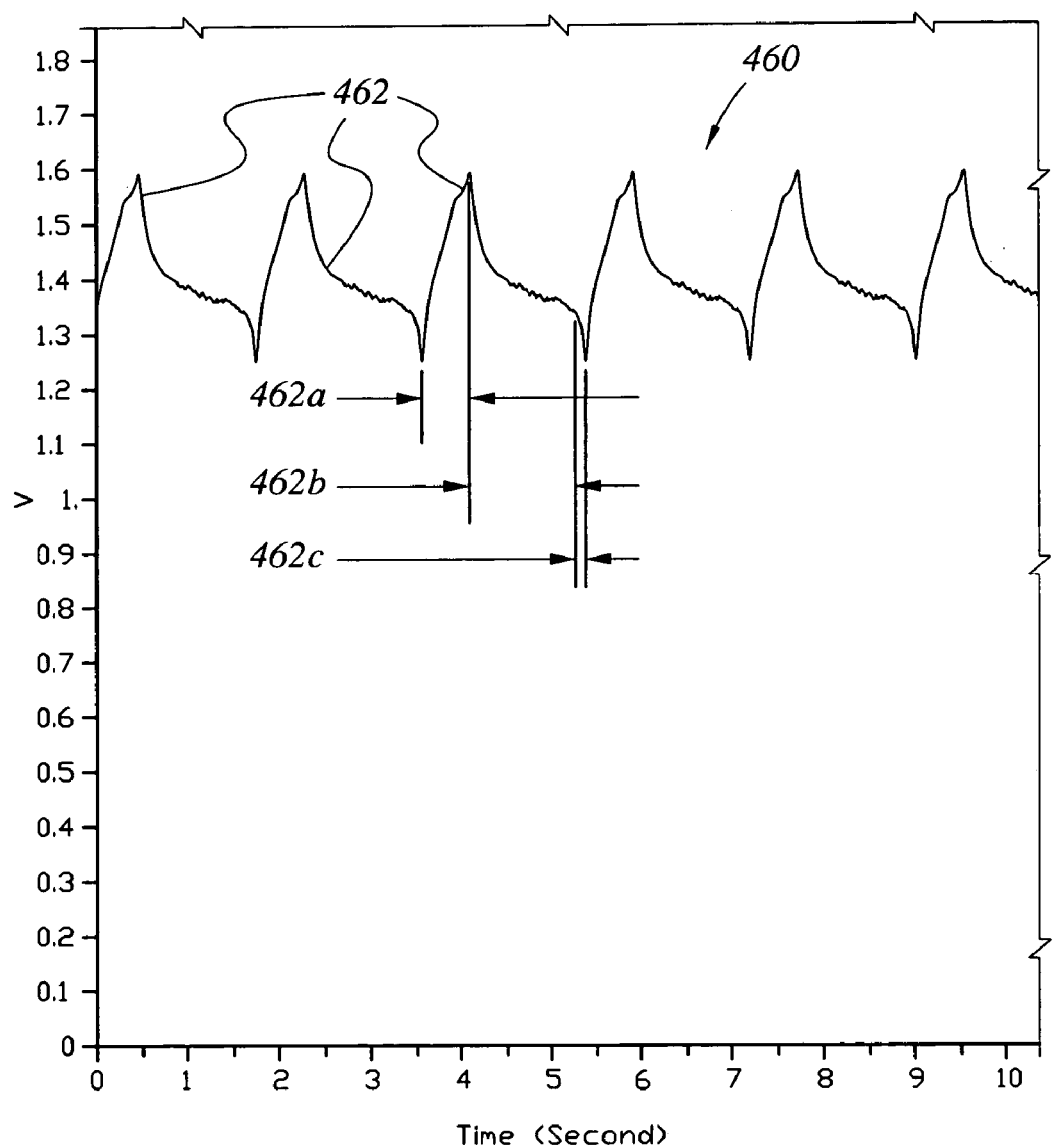

The wave forms of FIGS. 4A through 4F depict the bubble signatures of a series of different fuels, while the wave form of FIG. 4G depicts the bubble signature of water. The differing viscosities of the various liquids, which are influenced by their temperatures, primarily affect the bubble pulse frequency (once the pump has been adjusted to a constant setting). The pressure head of the liquid at the outlet end of the dip tube, i.e. the depth of the liquid, also affects the bubble pulse frequency, as it takes longer for the pump to generate the higher pressure needed to force a bubble from the end of the dip tube with a higher liquid pressure head. Surface tensions of the various liquids appear to have the greatest effect on the amplitudes of the wave forms.

FIG. 4A provides a graph illustrating the wave form or "bubble signature" of 87 octane unleaded gasoline, using the apparatus of the present invention. The bubble signature or wave form 400 of the graph of FIG. 4A is generated by the minute and rapid variations in the air or gas pressure within the dip tube line, e.g. line 226 of the apparatus 210 of FIG. 3, as the bubbles 236 exit the lower end 228 of the dip tube 226. As no filters, regulators, or other devices are installed in the lines 226 and 252 between the outlet end 228 of the dip tube 226 and the differential pressure sensor 254, the wave forms or bubble signatures are completely undamped, with the various minute pressure spikes and depressions being readily detectable. This wave form 400 is drawn as it would appear without a suppressor, e.g. suppressor 65 of the apparatus of FIG. 1, etc., installed in the system. It will be understood that the miniscule spikes or "noise" would be removed from the wave form when such a suppressor is installed, while still showing the major portions of the wave form 400 as described below.

These pressure variations are detected by the differential pressure sensor, e.g. sensor 254 in FIG. 3, and transmitted to the controller 258 and thence to the computer or processor 260. The wave forms or bubble signatures may then be read on a conventional oscilloscope or computer monitor 270, generally as indicated in FIG. 3. The horizontal axis represents time, and the vertical axis represents voltage generated by the differential pressure sensor as it senses the pressure variations. It will be understood that such a monitor or other display device may be provided with the systems 10 and 110 respectively of FIGS. 1 and 2 as well, if so desired. In any event, the systems 10 and 110 include means for differentiating the various bubble signatures of various liquids from one another (e.g. software programmed into the processor or controller, or electronic circuitry), for purposes explained further below.

The bubble signature 400 of FIG. 4A comprises a series of individual cycles 402. Each cycle 402 has three general phases: A relatively short, steeply rising phase 402a, a more gradually descending phase 402b, and a shorter, more steeply descending phase 402c. These three phases 402, 402b, and 402c are generally equivalent respectively to the three phases illustrated in FIGS. 5A, 5B, and 5C, showing the outlet end 228 of the dip tube 226 and its temperature probe 221 with bubble 236 emission, in accordance with the apparatus 210 of FIG. 3. More accurately, the phase 402a is generally equivalent to the phase extending from the end of the cycle at FIG. 5C, through the instant shown in FIG. 5A and back to the instant shown in FIG. 5B; the phase 402b is generally equivalent to the bubble formation phase, one instant of which is shown in FIG. 5B; and the phase 402c is generally equivalent to the bubble completion and departure phase, one instant of which is shown in FIG. 5C.

The phase 402a of the wave form 400 of FIG. 4A develops as pressure increases in the dip tube, e.g. tube 226, and line 252 between the outlet end of the tube 226 and the differential pressure sensor 254, as pressure builds at the outlet end 228 of the tube 226 to push through the surface tension of the liquid. The air or gas pressure must first overcome the surface tension which causes the peak buildup of pressure in the dip tube. Once the surface tension is overcome, the bubble begins to form outside the outlet end or mouth 228 of the dip tube 226, generally as illustrated in FIG. 5B, and begins to push through the liquid at the outlet end of the tube 226. If there were no surface tension, the air or gas would seep past the edge of the mouth 228 of the tube 226 at a constant rate without forming a significant pressure buildup, with pressure in the tube 226 and line 252 remaining essentially constant. In other words, if there were no surface tension, there would be no bubble formation.

Phase 402b of the wave form 400 of FIG. 4A shows the pressure decreasing as the bubble begins to form outside the mouth 228 of the dip tube 226. This pressure reduction is due to the fact that the pressure required to break the surface tension in phase 402a is higher than that required to form the bubble. Phase 402b represents the descending slope of pressure as the bubble is being formed, with the surface tension beginning to reform around the bubble instead of extending across the outlet end 228 of the dip tube 226. Some positive pressure is of course still required to overcome the static pressure head due to the depth of the liquid, and the dynamic pressure due to the viscosity of the liquid. Liquid depth, i.e. pressure head, and viscosity appear to be the greatest factors affecting the wave form frequency, while the surface tension of the liquid appears primarily to affect the amplitude of the pressure variations detected by the present invention.

Phase 402c of the wave form 400 of FIG. 4A shows a very short, steep ending phase, representing the pressure drop associated with the portion of the cycle depicted in FIG. 5C. This short, steep pressure drop of phase 402C appears to be due to the completion of the spherical bubble 236, as the surface tension rapidly closes across the outlet end 228 of the tube 226 to completely enclose the newly formed bubble 236 at the end of the tube. This happens relatively rapidly, in comparison to the time required for the formation of another bubble at the end 228 of the tube 226.

During the period immediately following bubble release, i.e. the period between FIG. 5C and return to FIG. 5A to begin a new cycle, the pressure within the tube 226 may tend to resonate due to the sudden drop in pressure caused by the bubble release. This resonance or vibration of the air column is indicated by the third phase 402c in FIG. 4, with its somewhat irregular spikes and valleys. It will be appreciated that the resonance of the air column will be dampened to varying degrees by the liquid in the container, depending upon the nature of the specific liquid being used. A suppressor or damper, e.g. the device 65 of FIG. 1, may be installed in the system to further dampen these resonant spikes, if so desired.

It will be noted that the frequency of bubble generation is dependent upon the type of liquid being used, or more specifically upon the viscosity of the liquid, with surface tension and pressure head (depth) primarily affecting the amplitude of the wave form. The extremely fine resolution of the present system enables the user to determine which one of a number of different liquids is disposed at the lower end of the dip tube, according to the specific wave form or "bubble signature" generated.

In the example of FIG. 4A, the ten second span of time allows the formation of a total of 19.5 wave cycles across the width of the graph. This number is characteristic of 87 octane unleaded motor vehicle gasoline, as noted further above. The amplitude of the wave form or bubble signature, i.e. the maximum pressure developed at each cycle, is also quite consistent, as observation of the graph of FIG. 4A clearly indicates. However, these characteristics differ between different liquids, as noted above. The present inventor has found that the present inventive system is capable of discriminating between different grades or octane ratings of gasoline, as well as between other liquids.

FIG. 4B provides an illustration of a wave form or bubble signature 410 for 89 octane rating gasoline. The difference in additives to form the different octane ratings results in some differences in surface tension and viscosity between the two fuels of FIGS. 4A and 4B. The two wave forms 400 and 410 are quite similar in appearance, but it will be noted that there are differences. The primary difference between the two is the slightly lower frequency of about 19.25 cycles across the ten second span of the graph of FIG. 4B, or about ¼ cycle less than the wave form 400 of FIG. 4A. It will also be noted that the recovery period 410c is somewhat more regular than the equivalent period 402c for the 87 octane fuel of FIG. 4A. The amplitude of the various wave forms, as indicated by the voltage along the vertical left axis of each graph, also differs somewhat between the different liquids tested, but the difference may not be readily discernible in the case of closely related liquids.

FIG. 4C provides an illustration of a graph showing the wave form or bubble signature 420 for 93 octane equivalent motor fuel. The surface tension and viscosity of this fuel differs sufficiently from the fuels of FIGS. 4A and 4B, to produce a somewhat different wave form 420. Each of the individual cycles 422 has a series of three distinct phases, i.e. 422a, 422b, and 422c, as in the wave forms 400 and 410 respectively of FIGS. 4A and 4B. It will be noted that the frequency of the bubble signature 420 is somewhat lower than the wave forms or bubble signatures 400 and 410, i.e. there are only 18 cycles across the ten second span of the chart of FIG. 4C. The recovery period 422c is somewhat different as well. It will be appreciated that these differences are not only visible in graphic form, but can be detected by suitably programmed conventional electronic means.

FIG. 4D is an illustration of the bubble signature or wave form 430 generated by E-85 motor fuel, i.e. fuel of a mixture of 85% ethanol and 15% gasoline. The surface tension and viscosity of this fuel differ substantially from those of other fuels tested, as indicated by the bubble signature 430 of FIG. 4D. It will be noted that the frequency of the wave form 430 is considerably lower than the other fuels of FIGS. 4A through 4C, being only about 14 cycles per ten second period in FIG. 4D. It will also be noted that the descending phase of the cycle, i.e. immediately after bubble release, is somewhat longer than with other fuels. This may be due to the difference in viscosity of E-85 fuel in comparison to gasolines, but the surface tension of the primarily ethanol fuel enters into this as well.

FIGS. 4E and 4F respectively provide illustrations of wave forms or bubble signatures 440 and 450 for number one and number two diesel fuel. These two fuels have slightly different combustion characteristics and require some engine adjustments for optimum efficiency, depending upon which of the two fuels is used. It will be noted that the pressure drop phase 442b and 452b of the no. 1 and no. 2 diesel fuels is relatively long, in comparison to the fuels tested and graphed in FIGS. 4A through 4D. This appears to be a matter of viscosity with the relatively more viscous diesel fuels, but as in the cases of the other fuels tested, surface tension also plays a part. Another major difference in the two diesel fuels in comparison to the other fuels tested is the frequency. As in the cases of the other fuels, the frequency of the bubble signature is different. In the case of the no. 1 diesel fuel of the graph of FIG. 4E, only about 9.75 cycles are repeated in a ten second time span. With No. 2 diesel fuel, the frequency drops to only 9.65 cycles in ten seconds. These differences are readily detectable by conventional electronic discrimination circuitry and software.

Finally, FIG. 4G provides a graph showing the wave form or bubble signature for water, as a reference. The surface tension and viscosity of water differ considerably from those properties of the fuels tested and shown in FIGS. 4A through 4F. The surface tension in particular of water differs considerably from that of gasoline, being about twice as great as that of a typical gasoline. Accordingly, the wave form or bubble signature 460 produced using the present invention with water, is considerably different than the other bubble signatures of FIGS. 4A through 4F. Due to the surface tension of water, considerably greater pressure is required to force a bubble through the surface tension, to break away from the end of the dip tube. This is clearly indicated by the additional voltage required to produce the water bubble signature, on the order of 0.35 volts difference between the minimum and maximum voltages as shown in the graph of FIG. 4G across 462*a*. In comparison, most of the other fuels tested and shown in the graphs of FIGS. 4A through 4F have a maximum voltage difference of only about 0.07 to 0.10 volts. The wave form frequency is considerably lower for water than with other fuels as well, with water producing a bubble frequency of only about 5.4 cycles in ten seconds.

The present invention thus provides a device which is not only capable of measuring the depth of a liquid in a container or tank, but which is also capable of determining which of a large variety of liquids is disposed at the outlet end of the dip tube. The present invention has great utility in the detection of anomalous liquids in fuel tanks of various types, e.g. the detection of water in automobile or aircraft fuel tanks, as indicated by the water 70 in the sump 24 in FIG. 1, or water 170 in the bottom of the tank 112 in FIG. 2. The present system can also be used to check for blockages in the fuel system, e.g. ice in the sump 24, as there will be no pneumatic flow from the outlet 28 of the tube 26 in such a situation. The present system may be configured to recognize such a problem, if excessive pressure builds in the system to indicate such a blockage.

Conventional electronic circuitry and/or software can easily detect the differences in the wave forms illustrated in FIGS. 4A through 4G, as well as innumerable others. When an anomalous liquid, or ice, is detected at the bubble outlet end of the dip tube, the electronic circuitry can trigger an audio or visual alarm, e.g. the alarm 72 or 172 respectively of FIGS. 1 and 2, by known means to alert the operator of foreign matter in the fuel tank.

In conclusion, the present system provides sufficient resolution to be able to detect differences in different octane ratings of gasoline, as shown further above. Modern automobile engines are configured to operate optimally on a specific grade of fuel, and must be adjusted to run properly on a lower (or higher) grade. It is well known that operating an engine on a lower fuel octane rating than that for which it is designed can cause serious engine damage unless the engine is adjusted to accommodate those fuels. Many modern engines incorporate relatively costly knock sensors which automatically reduce throttle opening and/or retard the ignition timing to compensate for relatively low octane fuels. The present invention can be interfaced with the engine systems to perform the same function, while also performing the function of the fuel quantity gauge. The open loop circuitry of the present system, with its elimination of costly regulators, filters, etc., results in a device which is considerably less costly to produce than devices of the related art, and which may be economically installed in a variety of vehicles and systems.

The present invention also lends itself to installation in space heater tanks as well. Many accidents have occurred with such devices when they have been fueled with the incorrect type of fuel. The present device may be used to provide an alarm when the incorrect fuel is detected, and/or trip an ignition lockout which will prevent the heater from operating until the correct fuel is used. Much the same system could be applied to aircraft, with a circuit to disable the starter motor(s) if an incorrect fuel, or water, is detected in the fuel tank(s).

The present invention, with proper adjustment and resolution, may be used to detect the differences in innumerable different liquids, as noted further above. The present device may be adapted for use in blood typing or checking for iron deficiency, measuring the percentage of various ingredients in drinks, e.g., cream content of milk, percentage of solids in various drinks, etc., according to the electronic discrimination circuitry and/or software provided with the device. The economical construction of the present invention, with its lack of regulators and other relatively costly components, provides a dual purpose device which is economically on a par with conventional fuel gauge systems, but which provides considerably more information and versatility. The present liquid quantity indicator with its liquid identification capability will thus find widespread application in innumerable fields.

It is to be understood that the present invention is not limited to the embodiments described above, but encompasses any and all embodiments within the scope of the following claims.

I claim:

1. A liquid depth sensing system with liquid identification capability, comprising:
    a liquid container having at least one peripheral wall and a floor;
    a gas delivery dip tube extending into said container, said dip tube having an open lower end spaced at least slightly apart from the floor of said container;
    a pneumatic gas supply pump disposed externally to said container, and communicating with said dip tube;
    a differential pressure sensor communicating with said dip tube and with ambient pressure;
    a pump controller communicating electrically with said differential pressure sensor and with said pump;
    a liquid quantity and anomalous liquid detection processor communicating electrically with said controller;
    a liquid quantity indicator receiving signals from said processor; and
    an anomalous liquid annunciator communicating electrically with said processor.

2. The liquid depth sensing system with liquid identification capability according to claim 1, wherein said pump comprises a miniature pump having an electrically actuated pump drive integrally disposed therewith.

3. The liquid depth sensing system with liquid identification capability according to claim 1, further including an open loop pulse control circuit electrically connecting said pump and said pump controller, governing the pulse frequency of said pump in accordance with electrical signals from said pump controller.

4. The liquid depth sensing system with liquid identification capability according to claim 1, wherein said liquid container comprises a closed container further including a top, the sensing system further comprising a vent tube extending into said container, the vent tube being concentrically disposed about said dip tube and pneumatically connected to said differential pressure sensor.

5. The liquid depth sensing system with liquid identification capability according to claim 4, further including a vapor pressure sensor disposed between said vent tube and ambient atmosphere.

6. The liquid depth sensing system with liquid identification capability according to claim 4, further including a vapor temperature sensor disposed along said vent tube.

7. The liquid depth sensing system with liquid identification capability according to claim 1, wherein:
   said container is open to ambient atmosphere; and
   said differential pressure sensor is exteriorly vented relative to said container.

8. A liquid depth sensing system with liquid identification capability, comprising:
   a liquid container having at least one peripheral wall and a floor;
   a gas delivery dip tube extending into said container, said dip tube having an open lower end spaced at least slightly apart from the floor of said container;
   a miniature pneumatic gas supply pump and electrically actuated pump drive integrally disposed therewith, disposed externally to said container and communicating with said dip tube;
   a differential pressure sensor communicating with said dip tube and with ambient pressure;
   a pump controller communicating with said differential pressure sensor and with said pump;
   an open loop pulse control circuit electrically connecting said pump and said pump controller, governing the pulse frequency of said pump in accordance with electrical signals from said pump controller; and
   a liquid quantity indicator receiving signals from said processor.

9. The liquid depth sensing system with liquid identification capability according to claim 8, further including a liquid quantity and anomalous liquid detection processor communicating electrically with said controller.

10. The liquid depth sensing system with liquid identification capability according to claim 8, further including an anomalous liquid annunciator communicating electrically with said processor.

11. The liquid depth sensing system with liquid identification capability according to claim 8, wherein said liquid container comprises a closed container having a top, the system further comprising a tank vent tube extending into said container, the vent tube being concentrically disposed about said dip tube and pneumatically connected to said differential pressure sensor.

12. The liquid depth sensing system with liquid identification capability according to claim 11, further including a vapor pressure sensor disposed between said vent tube and ambient atmosphere.

13. The liquid depth sensing system with liquid identification capability according to claim 11 further including a vapor temperature sensor disposed along said vent tube.

14. The liquid depth sensing system with liquid identification capability according to claim 8, wherein:
   said container is open to ambient atmosphere; and
   said differential pressure sensor is exteriorly vented relative to said container.

15. A liquid depth sensing system with liquid identification capability, comprising:
   a closed liquid container having at least one peripheral wall, a floor, and a top;
   a gas delivery dip tube extending into said container, said dip tube having an open lower end spaced at least slightly apart from the floor of said container;
   a vent tube extending into said container, the vent tube being disposed concentrically about said dip tube;
   a miniature pneumatic gas supply pump disposed externally to said container, and communicating with said dip tube;
   an electrically actuated pump drive integrally disposed with said pump;
   a differential pressure sensor communicating with said dip tube and with said vent tube;
   a pump controller communicating with said differential pressure sensor and with said pump; and
   a liquid quantity indicator receiving signals from said processor.

16. The liquid depth sensing system with liquid identification capability according to claim 15, further including a liquid quantity and anomalous liquid detection processor communicating electrically with said controller.

17. The liquid depth sensing system with liquid identification capability according to claim 15, further including an anomalous liquid annunciator communicating electrically with said processor.

18. The liquid depth sensing system with liquid identification capability according to claim 15, further including an open loop pulse control circuit electrically connecting said pump and said pump controller, governing the pulse frequency of said pump in accordance with electrical signals from said pump controller.

19. The liquid depth sensing system with liquid identification capability according to claim 15, further including a vapor pressure sensor disposed between said vent tube and ambient atmosphere.

20. The liquid depth sensing system with liquid identification capability according to claim 15, further including a vapor temperature sensor disposed along said vent tube.

* * * * *